US00PP12641P2

(12) United States Plant Patent
Clark et al.

(10) Patent No.: US PP12,641 P2
(45) Date of Patent: May 21, 2002

(54) NECTARINE TREE NAMED 'ARRINGTON' CULTIVAR

(75) Inventors: John Reuben Clark; James Norman Moore, both of Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 14 days.

(21) Appl. No.: 09/688,048

(22) Filed: Oct. 13, 2000

(51) Int. Cl.[7] ..... A01H 5/00

(52) U.S. Cl. ..... Plt./190
(58) Field of Search ..... Plt./190

*Primary Examiner*—Bruce R. Campell
*Assistant Examiner*—Annette Para

(57) ABSTRACT

Description and specifications of a new and distinct nectarine tree variety which originated from seed produced by a hand pollinated cross of Arkansas Nectarine Selection 178 (non-patented) and Arkansas Nectarine Selection 232 (non-patented) is provided. This new nectarine variety can be distinguished by its very early fruit maturity, very firm non-melting flesh texture, high yield, excellent tree vigor, and attractive fruits with good flavor.

3 Drawing Sheets

SUMMARY OF THE INVENTION

The new and distinct variety of nectarine tree originated from a hand pollinated cross of Arkansas Nectarine Selection 178 (non-patented)×Arkansas Nectarine Selection 232 (non-patented) made in 1984 at the Arkansas Agricultural Experiment Station Fruit Substation at Clarksville, Ark. The parent plants used in this hybridation have not been named and released and are unavailable in commerce.

Plants and fruit of this new variety differ phenotypically from its parents. The new variety produces larger fruits, with better flavor, and more vigorous and productive trees than the parent Arkansas Nectarine Selection 178, and is earlier ripening, more vigorous, more productive, and produces larger fruits than the parent Arkansas Nectarine Selection 232. Both the parents and the instant variety are the genus and species *Prunus persica*.

The seeds resulting from this controlled hybridization were germinated in a greenhouse in the spring of 1985 and planted in a field on the Arkansas Agricultural Experiment Station in Clarksville, Ark. The seedlings fruited during the summer of 1989 and one, designated Arkansas 417, was selected for its very early ripening, attractive fruits, firm fruit texture, and good fruit quality. During 1989, the original plant selection was propagated asexually, at the above noted location, by budding onto standard peach rootstock variety 'Lovell' (non-patented) and a test plot of two plants was established. Subsequently, larger test plantings have been established with asexually multiplied plants (propagated at the same location by budding) at two additional locations in Arkansas (Clarksville, and Hope, Ark.).

The new variety has been asexually multiplied by budding several times at this same location since 1989 by budding onto 'Lovell' peach rootstock and no incompatibility with this peach rootstock has occurred following budding. During all asexual multiplication, the characteristics of the original plant have been maintained and no aberrant phenotypes have appeared.

Plants of the new variety are vigorous and productive. Trees are standard in size in comparison to other nectarine or peach trees (*Prunus persica*), well branched and symmetrical with an upright growth habit. Plants and fruit are moderately tolerant to peach bacterial spot, incited by *Xanthomonas campestris* pv. *pruni* (Smith) Dye. The new variety blooms in the spring an average of 3 days earlier than the 'Redgold' (U.S. Plant Pat. No. 1,329) and 'Summer Beaut' (U.S. Plant Pat. No. 4,093) varieties. No winter injury has been observed on wood or buds of the new variety in Arkansas test where minimum temperatures have reached −23° C. Chilling requirement to break dormancy is estimated to be 750 hours below 7° C.

Fruit of the new variety ripens very early, averaging 28 days earlier than the 'Redgold' variety, 18 days earlier than the 'Summer Beaut' variety, and 9 days earlier than the reference peach variety 'Redhaven' (non-patented). Average ripening date is June 24 in central Arkansas. Fruits are very firm at maturity and fruit quality is retained well on the tree after maturity for 5 to 7 days. Fruit yields are very good, and the new variety outyielded the 'Redgold' and 'Summer Beaut' varieties in all replicated test plantings in Arkansas. Yields are consistent from year to year.

The fruit of the new variety is round in shape, with light, bright red skin color over yellow ground color. Fruit size is medium, averaging 125.1 g, and is slightly smaller than the 'Redgold' and 'Summer Beaut' varieties. Careful management of crop load is required to enhance fruit size. The fruit is non-melting in texture and very firm at maturity, rating much more firm than the 'Redgold' and 'Summer Beaut' varieties. Storage ability of fresh fruit of the new variety is superior to both the 'Redgold' and 'Summer Beaut' varieties in that it is has firmer flesh at maturity resulting in longer storage capability. Fruit cracking has not been observed on the instant variety. The flesh of the fruit is a uniform yellow color with no red pigment present. The fresh fruit rates good in flavor and is especially good for a very early ripening nectarine. The flavor is sweet and mildly subacid, wtih a mild nectarine aroma. The soluble solids concentration averages 12.2% and exceeds 15.0% in some years.

The distinctive features of the new variety are its very early fruit ripening, very firm non-melting flesh texture, high yields, excellent tree vigor, and attractive fruits with good flavor.

The new variety has been named the 'ARRINGTON' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly as it is reasonably possible to make in a color illustration of this character.

DETAILED DESCRIPTION OF THE NEW VARIETY

The following is a detailed description of the botanical and pomological characteristics of the subject nectarine. Color data are presented in Royal Horticultural Society Colour Chart designations and are supplemented with readings from a Minolta Chroma Meter CR-200, version 3.0, which measures absolute chromaticity in tristimulus values L, a, and b. Calibration was performed using a standard white plate supplied by the manufacturer.

Where dimensions, sizes, colors and other characteristics are given, it is to be understood that such characteristics are approximations of averages set forth as accurately as practical.

The descriptions reported herein are from specimens grown at Clarksville, Ark. and are from trees grown in trickle (drip) irrigated orchards growing on a Linker fine sandy loam soil. The data were collected from eight-year old trees of the instant variety except yield data that were taken on five-year-old trees in a replicated test planting.

Tree:

*Size.*—Mature trees (5 years of age and older) average 3.4 m to 3.7 m in height and 4.7 to 5.6 m in spread or width and have an upright growth habit, as grown on 'Lovell' rootstock using an open-center training system commonly used on nectarines. Tree size is comparable to that of the 'Red Gold' and 'Summer Beaut' varieties.

*Growth.*—Very vigorous, symmetrical form, good canopy development. Vigor comparable to that of the 'Red Gold' and 'Summer Beaut' varieties.

*Productivity.*—Very good and consistent from year to year. Yield measured 43.5 kg/tree on five-year old trees and exceed the yield of 'Summer Beaut' of 30.8 kg/tree and 'Red Gold' of 16.7 kg/tree in a test planting of identical age and growing conditions.

*Cold hardiness.*—Wood and dormant buds hardy to −23° C.

*Disease resistance.*—Leaves and fruit moderately resistant to bacterial spot under growing conditions where bacterial spot infection is often very severe on susceptible genotypes. No bactericides were used in the development or evaluation of the instant cultivar. Evidence of bacterial spot infection less than that of 'Red Gold' and comparable in most years to that of 'Summer Beaut' in all years of evaluation. A commercial fungicide program was utilized in orchards used in the development and evaluation of the instant variety, thus no resistance to brown rot or scab, the other common diseases at Clarksville, Ark., was determined.

*Insect resistance.*—Insecticides were applied to orchards used in the development of the instant variety to control the common insects at the location including oriental fruit moth, plum curculio, stinkbug, tarnished plant bug, lesser peach tree borer and greater peach tree borer. Therefore no insect resistance was determined in the testing of the instant variety.

Foliage:

*Shoots.*—Glabrous. Mature shoot length 78.0 cm; diameter base 6.6 mm, midpoint 4.1 mm, terminal 1.7 mm. Mature shoot color adaxial side: Greyed Red Group (178A), L=39.43, a=26.61, b=12.33; Mature shoot color abaxial side: Yellow Green Group (145A).

*Leaves.*—Simple, alternate, glabrous, lanceolate, petiolate, deciduous. Venation pinnate; base acute to occasional oblique; terminal or apex acuminate; margin serrated. Mature leaf size: length 16.2 cm; diameter midpoint 3.72 cm. Leaf serrations, 6.20/cm. Mature leaf color: Abaxial-Yellow Green Group (147B), L=44.80, a=−10.85, b=18.22 and anthocyanin present on the midrib only (central vein) on mature leaves; Adaxial-Yellow Green Group (147A), L=39.49, a=−7.66, b=10.99 and anthocyanin present on midrib of mature leaves. Young leaf color: Abaxial-Yellow Green Group (146D), L=53.19, a=−17.74, b=33.43; Adaxial-Yellow Green Group (144B), L=47.17, a=−19.56, b=33.86; anthocyanin not present on abaxial or adaxial side of young leaves on midrib or other location. Mature leaf pedicel length: 9.0 mm; anthocyanin present on adaxial and abaxial sides of mature leaf petiole and absent on young leaf petiole. Leaf glands: globose, 2 per leaf, located at base of leaf blade near juncture with petiole. Leaf glands are 0.33 mm in width and 0.43 mm in length and color of glands is Greyed Orange Group (166A). Leaf scar beneath bud at the end of the growing season 4 mm wide.

*Buds.*—Flower buds ovoid in shape; size at the termination of the growing season 3 mm long and 2 mm wide; dormant flower bud color Greyed Orange Group (174 A). Number of leaf buds per 15 cm: 6.7. Number of flower buds per 15 cm: 10.3. Mature shoot internode length: base 4.7 mm, midpoint 5.8 mm, terminal 6.1 mm.

Bark (of mature trunk of tree):

*Color.*—Grey Group (201D); L=53.39, a=3.63, b=11.23.

Flowers: Bloom occurs prior to vegetative bud break; solitary to occasional double individual flowers at a single node; perfect; self-fertile.

*Date of bloom.*—First, Julian 63 (March 3); Full, Julian 86 (March 26).

*Size.*—Diameter fully open 18.1 mm.

*Type.*—Non-showy.

*Petal color.*—Red Group (55C), L=78.19, a=29.29, b=2.74.

*Petals per flower.*—5.

*Length of pistil.*—1.24 cm.

*Date of petal fall.*—Julian 92 (April 1).

*Stamens.*—Numerous with pollen present, fertile and abundant.

*Date of shuck split.*—Julian 107 (April 16).

Fruit:

*Size.*—Medium, avg. 125.1 g; diameter stem end 5.24 cm, equator 6.30 cm, blossom end 5.36 cm; length base to apex 5.88 cm.

*Shape.*—Round, symmetrical, without pronounced tip or suture bulge.

*Skin.*—Glabrous, attractive; ground color Yellow Orange Group (22A), L=68.62, a=13.58, b=54.68;

overcolor Red Purple Group (59A), L=34.96, a=39.74, b=15.75. Skin medium thick and tenacious to flesh.

*Flesh.*—Color: Yellow Orange Group (18A), L=66.63, a=8.49, b=51.72, uniform throughout. Texture: clingstone, non-melting. Very firm, and when measured by a fruit pressure tester (using a McCormick model FT327 fruit pressure tester, 11 mm diameter probe, McCormick Fruit Tree Co., Yakima, Wash.) had average firmness value of 5.3 kg. Quality: good flavor, mild nectarine aroma.

*Pedicel length.*—7.9 mm.

*Ripe date.*—June 24 (Julian 176) in west-central Arkansas. Ripening of individual fruits is uniform.

*Tendency of pit to split.*—Variable among years but a maximum of 10% split pits measured.

*Soluble solids.*—Avg. 12.2%, occasionally exceeds 15.0%.

*pH.*—3.4 (of undiluted juice extracted from fruit).

Pit/stone:

*Size.*—Length 3.02 cm; diameter (midpoint) 1.85 cm.

*Shape.*—Oblong with deep furrowing.

*Color.*—Greyed Orange Group (165B), L=49.58, a=24.21, b=23.85.

Kernel:

*Size.*—Length 16.8 mm; width 11.3 mm; diameter varies with dryness of the kernel but is up to 2 mm.

*Shape.*—Elliptical with a straight or slightly curved apiculate apex.

*Color.*—Greyed Orange Group (164A).

Uses: Fresh consumption, canned, frozen; not evaluated for drying or other uses.

The variety: The most distinctive features of the variety are its very early fruit maturity, very firm non-melting flesh texture, high yields, excellent tree vigor, and attractive fruits with good flavor.

We claim:

1. A new and distinct variety of nectarine tree, substantially as illustrated and described, characterized by its very early fruit maturity, very firm non-melting flesh texture, high yields, excellent tree vigor, and attractive fruits with good flavor.

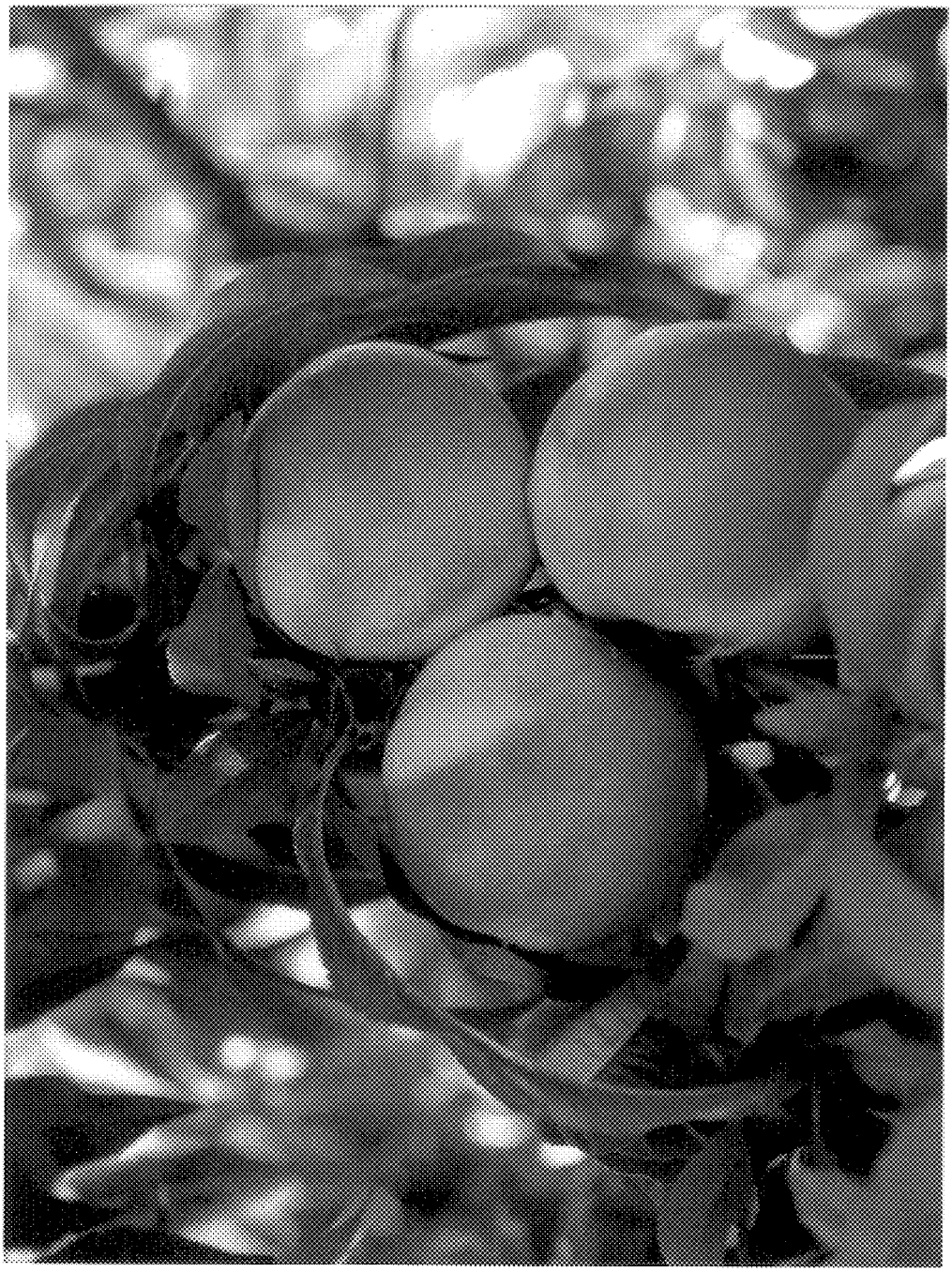

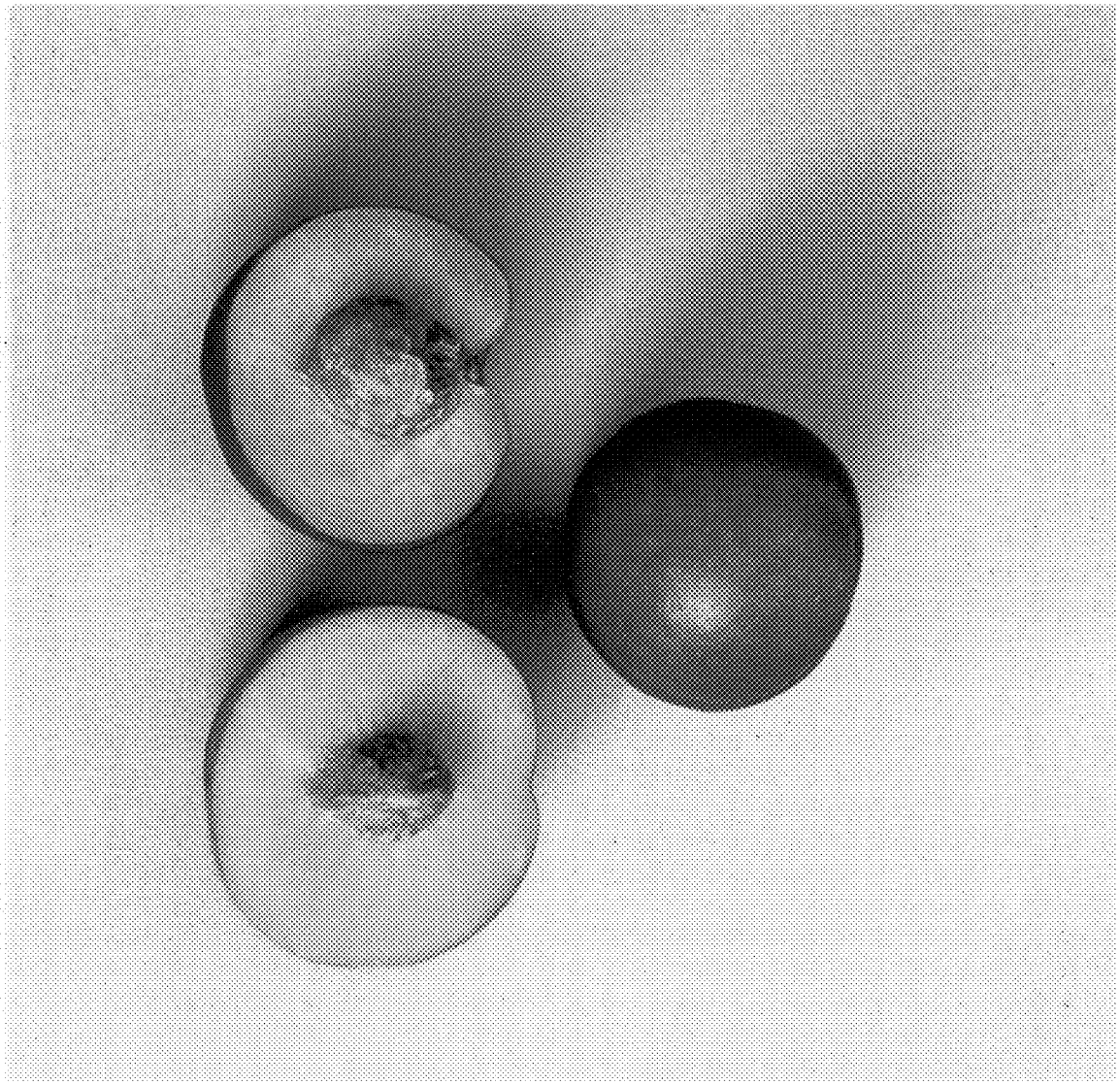

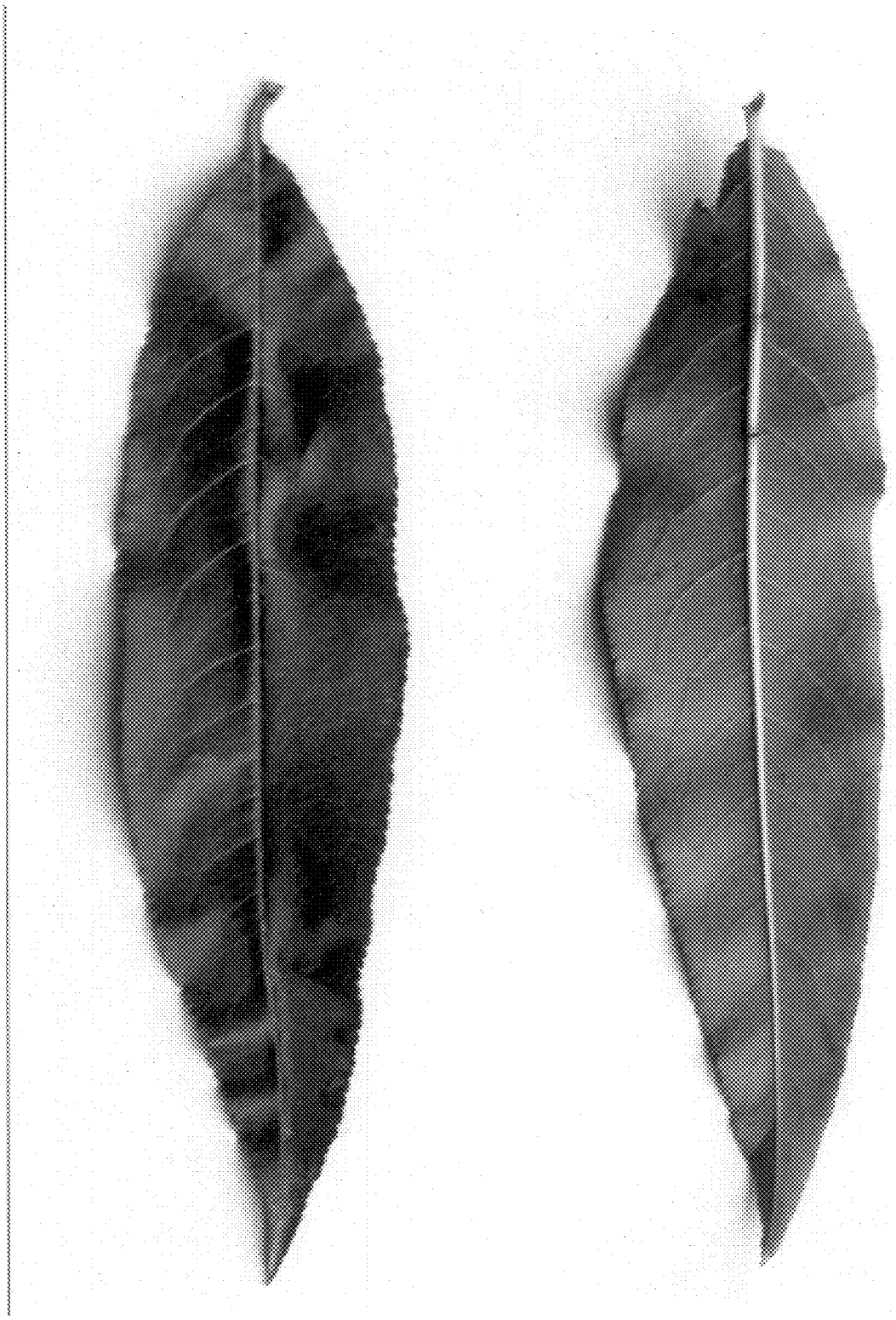

* * * * *